United States Patent
Shim et al.

(10) Patent No.: US 7,341,671 B2
(45) Date of Patent: *Mar. 11, 2008

(54) METHOD OF CONTROLLING THE GROWTH OF MICROORGANISMS

(75) Inventors: Sang-Hea Shim, Seoul (KR); Chung-Soo Kim, Kyungki-do (KR)

(73) Assignee: Acculab Co., Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 10/506,384

(22) PCT Filed: Mar. 5, 2003

(86) PCT No.: PCT/KR03/00423

§ 371 (c)(1),
(2), (4) Date: Mar. 2, 2005

(87) PCT Pub. No.: WO03/073848

PCT Pub. Date: Sep. 12, 2003

(65) Prior Publication Data

US 2005/0147528 A1    Jul. 7, 2005

(30) Foreign Application Priority Data

Mar. 5, 2002    (KR) .................... 10-2002-0011639

(51) Int. Cl.
*C02F 1/76* (2006.01)
(52) U.S. Cl. .................... 210/755; 210/756; 422/37
(58) Field of Classification Search ................ 422/37; 210/755, 756
See application file for complete search history.

(56) References Cited

U.S. PATENT DOCUMENTS

| | | | |
|---|---|---|---|
| 3,328,294 A | 6/1967 | Self et al. | |
| 3,767,566 A | 10/1973 | Rutkiewic et al. | |
| 4,071,463 A * | 1/1978 | Steinhauer | 510/370 |
| 4,557,756 A | 12/1985 | Teach et al. | |
| 4,557,926 A | 12/1985 | Nelson et al. | |
| 4,992,209 A | 2/1991 | Smyk et al. | |
| 5,683,654 A | 11/1997 | Dallmier et al. | |
| 5,688,515 A | 11/1997 | Kuechler et al. | |
| 5,795,487 A | 8/1998 | Dallmier et al. | |
| 5,942,126 A | 8/1999 | Dallmier et al. | |
| 5,961,879 A * | 10/1999 | Trigiante | 252/187.25 |
| 6,037,318 A | 3/2000 | Na et al. | |
| 6,110,387 A | 8/2000 | Choudhury et al. | |
| 6,136,205 A | 10/2000 | Dallmier et al. | |
| 6,270,722 B1 | 8/2001 | Yang et al. | |
| 6,303,038 B1 | 10/2001 | Sanders et al. | |
| 6,478,972 B1 | 11/2002 | Shim et al. | |
| 6,533,958 B2 | 3/2003 | Shim et al. | |

FOREIGN PATENT DOCUMENTS

EP    0 403 465 A1    12/1990

* cited by examiner

Primary Examiner—Gladys J P Corcoran
Assistant Examiner—Sean E Conley
(74) Attorney, Agent, or Firm—The Webb Law Firm, P.C.

(57) ABSTRACT

Disclosed is a method of preparing a biocide having improved durability of its biocidal activity as well as disinfection efficiency at an initial stage, comprising the steps of: (a) preparing stabilized alkali or alkaline earth metal hypochlorite having a pH at least 11 by mixing a chlorine oxidant including alkali or alkaline earth metal hypochlorite with a stabilizer in an alkali solution; (b) preparing a bromide ion source; and (c) adding the bromide ion source prepared in step (b) into the stabilized alkali or alkaline earth metal hypochlorite prepared in step (a). Also, a method of controlling the growth of microorganisms using a biocide prepared by the method of the present invention is disclosed.

3 Claims, No Drawings

METHOD OF CONTROLLING THE GROWTH OF MICROORGANISMS

TECHNICAL FIELD

The present invention relates, generally, to the control of contamination by microorganisms in water systems and, in particular, to a method for preparing a biocide comprising stabilized hypochlorite, which is made by reacting a chlorine oxidant including alkali or alkaline earth metal hypochlorite with a stabilizer, and a bromide ion source, and a method for controlling the growth of microorganisms.

BACKGROUND OF THE INVENTION

The formation of slime often occurs in water systems, such as a cooling water tower, an industrial water supply system, or a paper-making process, resulting from the growth and proliferation of bacteria, fungi, algae, etc. Such proliferation of microorganisms and slime formation bring about serious problems: in paper manufactories, it may give rise to slowdowns in operations and deterioration of products such as change in color of manufactured paper; reduction in the efficiency of heat exchange, which is critical for cooling capacity, in cooling systems may occur; the appearance of ornamental fountains may be damaged; and in cooling towers of buildings, especially, the genus *Legionella* may be rapidly spread, creating an unsanitary environment.

Oxidizing biocides and non-oxidizing biocides have been typically used to prevent the contamination of water system by microorganisms. Oxidizing biocides, which have oxidizing power, act as a biocidal agent against microorganisms by oxidizing their proteins, while non-oxidizing biocides work by inhibiting metabolism of microorganisms.

Examples of non-oxidizing biocides include isothiazolone, methylenebisisocyanate, glutaraldehyde, and quaternary ammonium. Such non-oxidizing biocides hold their biocidal activity for a longer period of time than oxidizing biocides, but when they are continuously supplied, microorganisms develop resistance to them, thereby lowering their effectiveness.

On the other hand, oxidizing biocides are typically prepared by chlorination and bromination, as represented by the following equations.

Chlorination

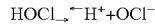

Bromination

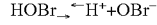

Of the two methods, the chlorination method is generally used for preparation of oxidizing biocides because it is low in cost. In this method, alkali or alkaline earth metal hypochlorite, such as sodium hypochlorite (NaOCl), is used as a source of HOCl or OCl⁻ to eliminate microorganisms growing in a variety of water systems including cooling water towers of buildings or petroleum plants, bleaching processes of paper-making factories, and swimming pools. However, the oxidizing biocides have a disadvantage in that they are unstable due to their high volatility. There have been efforts to solve these problems. Low volatile and stabilized N-chlorosulfamate can be prepared by reacting unstable hypochlorite with an equal molar ratio of sulfamic acid, as disclosed in U.S. Pat. No. 3,328,294 (hereinafter, referred to as '294 patent), and can be further stabilized along with the presence of a buffering agent capable of maintain pH between 4.5 and 8.5, as disclosed in U.S. Pat. No. 3,767,586 (hereinafter, referred to as '586 patent).

Although such chlorine biocides are inexpensive and can be prepared by a simple process, their disinfection efficiency may be reduced by a high pH or amines, and upon being used in large quantities, they can promote corrosion of metal, components of water systems, as well as releasing a lot of chlorine to atmosphere.

Oxidizing biocides prepared by the bromination method are, even under the condition of high pH or the presence of amines, more effective in controlling microorganism growth than those prepared by the chlorination. However, just like hypochlorite, hypobromite, as a product of the bromination, is also not stable under conventional storage conditions. Thus, to establish the stability of hypobromite during storage, processes for preparing stabilized hypobromite in U.S. Pat. No. 6,037,318 (hereinafter, referred to as '318 patent) have been proposed, the right to which have been transferred to the Procter & Gamble Company, and U.S. patents including U.S. Pat. Nos. 5,683,654; 5,795,487; 5,942,126; and 6,136,205.

As described especially in U.S. Pat. No. 5,795,487 (hereinafter, referred to as '487 patent), alkali or alkaline earth metal hypobromite in the unstable state, which is prepared by mixing alkali or alkaline earth metal hypochlorite and a water soluble bromide ion source, can be stabilized by employing an alkali metal sulfamate as a stabilizing agent.

Although the stabilized alkali or alkaline earth metal hypobromite prepared by the process of '487 patent shows an excellent biocidal efficiency, the level of total halogen residual which is a measure of an effective ingredient typically drops sharply at an initial phase of the reaction because hypochlorite reacts with a bromide ion source. Thus, with the passage of time, the biocidal efficiency of the hypobromite is rapidly reduced, thus requiring a continuous supply of a great quantity of expensive hypobromite, to maintain biocidal efficiency in water systems.

'318 patent discloses a stabilized hypobromite solution prepared by reacting an aqueous solution of alkali or alkaline earth metal hypochlorite with sulfamic acid as a stabilizing agent at pH below 11, adding to the solution water-soluble bromide ion source, and adjusting pH to about at least 13.

However, the process provided in '318 patent has a disadvantage. Because sulfamic acid used as a stabilizer becomes a strong acid upon being dissolved in water, addition of hypochlorite into a solution of sulfamic acid induces the release of gaseous chlorine, which is an effective ingredient, causing a large reduction in disinfection efficiency, as well as a harsh working environment for preparation of biocides. Moreover, owing to increased temperature by released heat during preparation, as well as the gas generation, pressure is increased. Consequently, the process mentioned in '318 patent is hard to apply in industry. In addition, since the hypochlorite added to the aqueous solution of the stabilizing agent is having a pH not exceeding about 11, the added bromide ion source immediately reacts with hypochlorite to form hypobromite, causing a problem in that its biocidal activity is not maintained for a long period of time.

As disclosed in U.S. Pat. No. 6,270,722 (hereinafter, referred to as '722 patent), stabilized hypobromite can be also prepared by mixing a stabilizing agent and a bromide ion source and adding hypochlorite to the mixture. In this patent, in order to produce a stabilized hypobromite, a stabilizer is, primarily, mixed with a bromide ion source, followed by supplementing with a sodium hypochlorite solution at a pH below about 7 and at below 80° F., and adjusting the pH of the mixture to at least 13 using an alkaline source such as a sodium hydroxide. The resulting product is characterized by an amber color and comprises about 90% of oxidizing bromine compounds, and has a biocidal effect similar to a biocide prepared according to '487 patent (STABREX™, Nalco Chemical Company), indicating that the resulting product is, like the commercially available biocide, a stabilized hypobromite, and when sodium hypochlorite is added into a mixture of bromide ion and a stabilizer having a pH below 7, bromide ion immediately reacts with sodium hypochlorite. Although the biocide prepared according to '722 patent is as effective against microorganisms as one manufactured according to '487 patent, the level of total halogen residual which is a measure of an effective ingredient is rapidly consumed, causing sharp reduction in the biocide's antibacterial activity with the passage of time. Therefore, it is required for a great quantity of the biocide to be supplied to maintain its bactericidal activity for a long time.

Also, stabilized hypobromite can be produced through prior addition of bromide ion and a stabilizer to periodically supplement sodium hypochlorite in swimming pools, as disclosed in U.S. Pat. No. 6,110,387 (hereinafter, referred to as '387 patent).

'387 patent teaches that the growth of microorganisms in swimming pools can be controlled by first adding bromide ion and a stabilizer and then periodically introducing a suitable chlorine biocide. Generally, since water of a swimming pool is at a neutral pH ranging from 7 to 8, bromide ions previously existing in a swimming pool react with hypochlorite, which is generated from a later-added chlorine oxidant, to form unstable hypobromite, and the unstable hypobromite reacts with pre-existing sulfamic acid, resulting in production of stabilized hypobromite. This method is very useful in water systems with no circulation of water, such as swimming pools, and features biocidal activity as effective as the biocide mentioned in '487 patent, but not in circulating water systems having continuous air contact, such as cooling water towers in plants, because of the large loss of the volatile chlorine biocide.

On the other hand, in order to provide stability of hypobromite during storage and convenience in its use, some methods for preparing it in a tablet form are mentioned in U.S. Pat. Nos. 4,557,756, 4,557,926, and 5,688,515 (hereinafter, referred to as '515 patent), and it is now commercially available as Towerbrom™. Especially, '515 patent describes water stable tablets for disinfecting recirculating water systems, comprising chlorinated isocyanurates, sodium bromide, and a stabilizer, in which the stabilizer is compatible, i.e., unreactive, with chlorinated isocyanurates, giving structural integrity to the tablets upon exposure to water and allowing the tablets to dissolve in water at relatively uniform and commercially acceptable rates, and capable of binding active chlorine generated by chlorinated isocyanurates, producing chlorinated stabilizer capable of storing active chlorine. Upon the tablets being immersed in water, the chlorinated stabilizer is able to slowly release active chlorine thanks to its lower solubility in water than chlorinated isocyanurates, and the active chlorine reacts with sodium bromide to generate hypobromite.

The method mentioned in '515 patent provides a biocide with an excellent efficiency. However, it is not convenient and economical in the views of requiring a specific supply equipment to maintain a constant concentration of active chlorine, and using an expensive chlorine oxidant as an active chlorine source.

DISCLOSURE OF THE INVENTION

The intensive and thorough research for control of the growth of microorganisms in water systems using stabilized hypochlorite and a bromide ion source, conducted by the present inventors with an aim to solve the problems encountered in prior arts, and recognizing the fact that prior addition of a stabilizer into an aqueous solution of hypochlorite to promote formation of stabilized hypochlorite and addition of bromide ion thereafter can, despite of low level of free halogen residual in the initial stage, bring about its gradual increase with the passage of time and thus the long retention of disinfection efficiency, as disclosed in Korean Pat. No. 0339129, U.S. Pat. No. 6,478,972, resulted in the finding that both initial biocidal activity and maintenance of biocidal activity for a long period of time, namely, durability, can be achieved by properly regulating the release rate of free halogen residual through the suitable control of pH in a reaction system.

Thus, it is an object of the present invention to provide a process for preparing a biocide stable in water systems through its low volatility and having an excellent biocidal activity, and capable of maintaining its biocidal activity for a long period of time, comprising stabilized alkali or alkaline earth metal hypochlorite and a water-soluble bromide ion source.

It is another object of the present invention to provide a method of controlling the growth of microorganisms using a biocide prepared by the above method.

In accordance with an aspect of the present invention, there is provided a method of preparing a biocide, comprising the steps of: (a) preparing stabilized alkali or alkaline earth metal hypochlorite having a pH at least 11 by mixing a chlorine oxidant including alkali or alkaline earth metal hypochlorite with a stabilizer selected from the group consisting of acid amide derivatives of carbonic acids, carboxylic acids, amino acids, and sulfuric acids in an alkali solution; (b) preparing a bromide ion source; and (c) adding the bromide ion source prepared in step (b) into the stabilized alkali or alkaline earth metal hypochlorite prepared in step (a).

In accordance with another aspect of the present invention, there is provided a method of controlling the growth of microorganisms, comprising the steps of: (a) preparing stabilized alkali or alkaline earth metal hypochlorite having a pH at least 11 by mixing a chlorine oxidant including alkali or alkaline earth metal hypochlorite with a stabilizer selected from the group consisting of acid amide derivatives of carbonic acids, carboxylic acids, amino acids, and sulfuric acids in an alkali solution; (b) preparing a bromide ion source; and (c) sequentially or simultaneously introducing the stabilized alkali or alkaline earth metal hypochlorite prepared in step (a) and the bromide ion source prepared in step (b) into a habitat of microorganisms to raise the level of total halogen residual up to 0.1 to 10 ppm.

BEST MODES FOR CARRYING OUT THE INVENTION

The present invention is directed to a method of preparing a biocide based on stabilization of an alkali or alkaline earth metal hypochlorite using a stabilizer and bromide ion source, while maintaining the biocide at pH at least 11. It is critical that the biocide should be maintained at pH at least 11 for the following reasons. When a stabilizer such as organic sulfamic acid is added to a solution of alkali or alkaline earth metal hypochlorite, such as sodium hypochlorite or potassium hypochlorite, an increase in temperature as well as a remarkable reduction in pH may occur resulting from neutralization of the alkali solution by production of hypochlorous acid with the dissolved sulfamic acid. Thereby, the lowered pH breaks the equilibrium state of the reaction, and thus the reaction proceeds toward the generation of gas, including chlorine, leading to the reduction in the content of available chlorine.

Therefore, according to the present invention, a stabilized aqueous alkali or alkaline earth metal hypochlorite solution is prepared by primarily dissolving a stabilizer in a alkali solution having a pH of at least 11, and then adding a chlorine oxidant including alkali or alkaline earth metal hypochlorite into the solution, thus preventing the reduction in total chlorine residual level in the reaction mixture and thus maintaining chloride residue close to its theoretical maximum value. Thus, despite the increase of temperature caused by neutralization reaction of the alkali solution (e.g., sodium hydroxide solution) by the employed stabilizer before introduction of a solution of sodium hypochlorite, it is possible to minimize the loss of available chlorine as well as to ensure no generation of gas, including chlorine, thanks to the absence of unstabilized hypochlorite, and to prevent the reaction of the stabilized hypochlorite with a bromide ion source before application to water systems and thus maintain them in an unreacted mixed state, and to simplify biocide preparation processes.

In the accordance with the present invention, there is provided a method of preparing a biocide, comprising the steps of: (a) preparing stabilized alkali or alkaline earth metal hypochlorite having a pH at least 11 by mixing a chlorine oxidant including alkali or alkaline earth metal hypochlorite with a stabilizer selected from the group consisting of acid amide derivatives of carbonic acids, carboxylic acids, amino acids, and sulfuric acids in an alkali solution; (b) preparing a bromide ion source; and (c) adding the bromide ion source prepared in step (b) into the stabilized alkali or alkaline earth metal hypochlorite prepared in step (a).

In the present invention, since the separately prepared bromide ion source is added into the stabilized aqueous alkali or alkaline earth metal hypochlorite solution of which pH has been maintained at least 11, thereby maintaining each ingredient in an unreacted state, the resulting biocide composition is characterized by existing in a state of initial low biocidal activity as well as in the enhanced state of durability.

When the biocide composition is delivered into water systems having a pH ranging from 8 to 9, the stabilized alkali or alkaline earth metal hypochlorite and the bromide ion source react to generate hypobromite which has a strong biocidal activity.

Because the stabilized hypochlorite serves as a reservoir of active chlorine, upon being delivered into a water system requiring disinfection, its reaction rate with bromide ion can be variously regulated according to pH, temperature, retention time, and its concentration in the water system.

Therefore, in the present invention, it is not necessary for hypochlorite and the bromide ion source to react in a molar ratio of 1:1, like in the conventional methods. Instead, the stabilized hypochlorite in the present invention allows the addition amount of the bromide ion source to be flexibly modified according to the degree of contamination of water systems. Therefore, it is possible to greatly reduce the consumed amount of expensive bromide ion source, and to maintain its biocidal activity for a long period of time, offering economical and effective control of microorganism growth in water systems.

In accordance with the present invention, in order to prevent generation of gaseous chlorine, reduction in total available chlorine residual content, and production of hypobromite, alkali or alkaline earth metal hypochlorite should be stabilized using a stabilizer under a condition of pH at least 11, and most preferably, at least 13.

Such maintenance of pH value may be achieved by the stabilization reaction accomplished in an alkali solution. Especially, any of all alkali solutions, and most preferably, a sodium hydroxide solution, can be used to maintain the pH value of at least 11.

In addition, the method of preparing a biocide of the present invention may further comprise two steps of: (d) lowering pH of the mixture prepared in step (c) to 5, and most preferably, 8; and (e) raising the pH to at least 11, and most preferably, at least 13, by adding an alkali solution.

As described above, the initial biocidal activity of the biocide prepared according to the present invention may be enhanced by lowering pH of the mixture, which is prepared in step (c) by mixing the stabilized alkali or alkaline earth metal hypochlorite solution with the bromide ion source, to pH 5, and most preferably, pH 8, allowing production of hypobromite having biocidal activity through the reaction between the alkali or alkaline earth metal hypochlorite and the bromide ion source in a certain pH range, with no generation of gaseous chlorine.

Upon lowering pH of the mixture as described above, the mixture solution typically turns light yellow in color with the transition of bromide ion to bromine, and the pH of the mixture should be then raised to at least 11, and most preferably, at least 13 by adding an alkali solution to obtain stability during storage, retaining the light yellow color. A biocide prepared by this method may have improved initial biocidal activity as well as a simplified preparation process and maintenance of biocidal activity for a longer period of time than the conventional biocides. If the pH is lowered to below 5 by adding acid (e.g., hydrochloric acid), the generation of gas including chlorine occurs just like the conventional methods, which are performed by adding sulfamic acid into a sodium hypochlorite solution. The method of the present invention does not generate gas in addition to making it possible to control the balance between initial biocidal activity and durability of biocidal activity, depending on adjusted pH value. That is, if the pH of the mixture is continuously maintained at least 11 without the step of adjusting the pH to 5, a biocide having an excellent durability and low initial biocidal activity is provided. In contrast, if the pH is lowered to a range generating no gaseous chlorine, the resulting biocide may show improved initial biocidal activity, whereas reduction in durability, but which is still relatively longer than the conventional biocides.

As described above, the method of the present invention is accomplished while maintaining the stabilized hypochlorite along with the bromide ion, in an unreacted state, thus not producing hypobromite, despite mixing of the two ingredients.

Conventional methods provide oxidizing biocides only having high initial biocidal activity without the consideration of durability of biocidal activity by producing hypobromite in advance through prior reaction of hypochlorite with bromide ion to form hypobromite having biocidal activity, followed by stabilization of the hypobromite in the presence of a stabilizer. However, in the present invention, hypochlorite is primarily stabilized using a stabilizer, and bromide ion is then added, giving enhanced durability as well as disinfection efficiency at an initial stage.

Namely, the stabilized hypochlorite, under a condition of pH below 11, reacts with water-soluble bromide ion to produce stabilized hypobromite, whereas, at pH over 11, the reaction is maximally inhibited. Upon being delivered into a water system having a low pH, the stabilized hypochlorite, serving as a reservoir of chlorine, releases available chlorine and reacts with bromide ions, whereby the reaction rate depends on an environment of water systems, such as pH, or temperature. In the accordance with present invention, the method comprising the steps of (a), (b), and (c) may provide a biocide having relatively lower initial biocidal activity than the conventional methods, but capable of maintaining its biocidal activity for a long period of time. Moreover, when steps (d) and (e) are further performed after steps (a) to (c), the resulting biocide may have initial biocidal activity as effective as those prepared by the conventional methods, by adding a simple step of lowering pH using a acidic solution, in addition to having increased durability of its disinfection efficiency. Moreover, the biocidal activity at an initial stage, and the durability, will vary depending on the extent to which the pH is lowered using an acidic solution.

The alkali or alkaline earth metal hypochlorite useful in the present invention may be selected from the group consisting of sodium hypochlorite, potassium hypochlorite, lithium hypochlorite, magnesium hypochlorite, calcium hypochlorite, a chlorinating agent, such as trichloroisocyanuric acid, sodium dichlorocyanuric acid, or dichlorohydantoin, and mixtures thereof, and most preferably, sodium hypochlorite or calcium hypochlorite.

Examples of the bromide ion source useful in the present invention include sodium bromide, potassium bromide, lithium bromide, chlorine bromide, and bromine, and most preferably, sodium bromide.

The stabilizer may be selected from the group consisting of acid amide derivatives of carbonic acid, carboxylic acid, amino acid, sulfuric acid, or phosphoric acid, and the acid amide derivatives are exemplified by urea, thiourea, creatinine, mono or di-ethanolamine, organic sulfonamide, biuret, sulfamic aicd, organic sulfamate, melamine, etc. In an aspect of economics and effectiveness, sulfamic acid is most preferable as a stabilizer.

In accordance with the present invention, a stabilized aqueous hypochlorite solution is prepared by reacting a chlorine oxidant with a stabilizer in a molar ratio of 1:9 to 9:1, and most preferably, 1:1. The stabilized aqueous hypochlorite solution is supplemented with a bromide ion source in a molar ratio of 1:10 to 50:1, and more preferably, 1:1 to 20:1. Herein, the content of each ingredient depends on the degree of contamination.

A biocide prepared according to the method of the present invention is, preferably, added to water systems in the level of 0.1 to 10 ppm total halogen residual, and more preferably, 0.2 to 5 ppm.

In addition, a biocide prepared according to the method of the present invention may further comprise a corrosion or scale inhibitor.

Examples of the anti-corrosion agent may include an anodic corrosion inhibitor, such as chromate, nitride, orthophosphate, silicate, or molybdate, and a copper corrosion inhibitor, such as mercaptobenzothiazole, benzothiazole, or tolyltriazole. Useful are organophosphates and acryl polymers as the scale inhibitor. The organophosphates are exemplified by triethanolamine phosphate (TEAP), aminotrimethylene phosphonic acid (AMP), 1-hydroxyethylidene-1,1-diphosphonic acid (HEDP), 2-phosphonobutane-1,2,4-tricarboxylic acid (PBTC), etc. Examples of the acryl polymers may include homo-acryl polymers, acryl co-polymers, and acryl tri-polymers.

A biocide prepared according to the method of the present invention can be used to prevent the growth of microorganisms in water systems, which include swimming pools, hot springs, ponds, water slides, and industrial water systems, such as cooling towers of buildings or plants, paper-making processes, wastewater recycling systems, gas scrubber systems, freshwater systems, or air washer systems, but are not limited to those, and the method and the biocides prepared using the same can be applied to any kind of water systems.

Having generally described this invention, a further understanding can be obtained by reference to certain specific examples which are provided herein for purposes of illustration only and are not intended to be limiting unless otherwise specified.

EXAMPLES

For use as a control, stabilized hypobromite was prepared according to the method disclosed in '487 patent, which is also commercially available as STABREX™ prepared by Nalco Chemical Company. Sodium hypochlorite (NaOCl) was diluted in water, and the diluted solution was titrated by the DPD-FAS method, and the available chlorine level was detected to be 15%. 42.4 g of the NaOCl solution was added to 20.5 g of a 45% NaBr solution to form unstabilized hypobromite. A sulfamate solution was prepared by mixing 9.6 g of sulfamic acid, 14 g of water, and 13.2 g of 50% NaOH. The sulfamate solution was added with stirring to the unstabilized hypobromite solution, generating a stabilized hypobromite solution (hereinafter, referred to as 'Biocide A').

Also, another biocide was prepared by the method disclosed in '318 patent. 26.5 g of a hypochlorite solution, of which available chlorine level is 11%, was added to 61 g of water, followed by sequential addition of 4.5 g of sulfamic acid, which dissolved completely. This solution was found to have pH below 1, and a lot of gas was generated during the reaction. The resulting solution was supplemented with 1 g of sodium bromide, and, after the sodium bromide was dissolved completely, further supplemented with 6.1 g of a 50% sodium hydroxide solution to adjust pH to 13.5, giving a biocide (hereinafter, referred to as 'Biocide B').

Using the method of the present invention, a biocide was prepared as follows. An alkali solution was prepared by adding 13.2 g of a 50% NaOH solution to 31.5 g of water. Added to the alkali solution was 9.6 g of sulfamic acid, and, after the sulfamic acid dissolved completely, 42.4 g of a NaOCl solution, producing a stabilized hypochlorite solution, after which 3 g of a aqueous 45% NaBr solution was added, giving a biocide (hereafter, referred to as 'Biocide C').

To prepare 'Biocide D', hydrochloric acid was primarily added to the 'Biocide C' with adjusting pH to 7.5. In this case, no generation of gas was found, and color was detected to change to yellow. Thereafter, the solution was adjusted to pH 13.5 using a sodium hydroxide solution while maintaining yellow color.

Of the biocides prepared as described above, it is preferable that the halogen content is theoretically the same as each other, but it was believed that no modification to the methods disclosed in the prior arts is necessary. Accordingly, biocides used as controls in embodiments of the present invention were prepared according to the method described in prior arts, resulting in that 'Biocide B' has less available halogen than 'Biocide A', 'Biocide C', and 'Biocide D'.

In order to investigate the biocidal activity of the biocides against microorganisms, a beaker test was performed. River water (pH 7.8) was added to a beaker, and a biocide was delivered to the water. The level of biocide residual according to the passage of time was determined by measuring the content of total halogen residual using the DPD-FAS method. Population of microorganisms was investigated using 3M petrifilm (aerobic count plate) after an incubation of 48 hours at 32° C. The water was maintained at 30° C., and, with the passage of time, a portion of the water was collected to investigate the level of total halogen residual and the population of microorganisms. The term 'total halogen residual level', as used herein, refers to the concentration of all compounds containing halogen, which are capable of serving as biocides.

Comparative Example 1

'Biocide A' was added to river water (pH 7.8) in a beaker in a variety of concentrations, and the antibacterial activity of 'Biocide A' was measured as described above. As apparent in Table 1, microorganism population was remarkably reduced when the water was treated with 'Biocide A' in an amount of over 100 ppm.

TABLE 1

| Concentration of 'Biocide A' (ppm) | Number of Surviving Bacteria After 1 day (CFU/ml) |
|---|---|
| 0 | 1,600,000 |
| 25 | 1,000,000 |
| 50 | 300,000 |
| 100 | 50,000 |
| 150 | 8,000 |
| 200 | 600 |
| 250 | 0 |

Note:
CFU (Colony Forming Unit) means viable bacteria population

Comparative Example 2

'Biocide B' was added to river water (pH 7.8) in a beaker in a variety of amounts, and the antibacterial activity of 'Biocide B' was measured as described above. The results are shown in Table 2, below. As shown in Table 2, the microorganism population was remarkably reduced when the water was treated with 'Biocide B' in an amount of over 150 ppm.

TABLE 2

| Concentration of 'Biocide B' (ppm) | Number of Surviving Bacteria After 1 day (CFU/ml) |
|---|---|
| 0 | 1,600,000 |
| 25 | 1,300,000 |
| 50 | 1,000,000 |
| 100 | 600,000 |
| 150 | 200,000 |
| 200 | 20,000 |
| 250 | 2,000 |

Example 1

'Biocide C' was added to river water (pH 7.8) in a beaker to a variety of concentrations, and the antibacterial activity of 'Biocide C' was measured as described above. The result is shown in Table 3, below. As shown in Table 3, the microorganism population was remarkably reduced when the water was treated with 'Biocide C' in an amount of over 50 ppm, demonstrating that 'Biocide C' has a strong antibacterial activity.

TABLE 3

| Concentration of 'Biocide C' (ppm) | Number of Surviving Bacteria After 1 day (CFU/ml) |
|---|---|
| 0 | 1,500,000 |
| 25 | 900,000 |
| 50 | 300,000 |
| 100 | 80,000 |
| 150 | 10,000 |
| 200 | 5,000 |
| 250 | 1,000 |

Example 2

'Biocide D' was added to river water (pH 7.8) in a beaker to a variety of concentration, and the antibacterial activity of 'Biocide D' was measured as described above. The result is shown in Table 4, below. As shown in Table 4, the microorganism population was remarkably reduced when the water was treated with 'Biocide C' in an amount of over 50 ppm, showing that 'Biocide D' has a strong antibacterial activity.

TABLE 4

| Concentration of 'Biocide D' (ppm) | Number of Surviving Bacteria After 1 day (CFU/ml) |
|---|---|
| 0 | 1,800,000 |
| 25 | 1,200,000 |
| 50 | 200,000 |
| 100 | 60,000 |
| 150 | 20,000 |
| 200 | 10,000 |
| 250 | 4,000 |

Example 3

In order to compare the antibacterial activities of 'Biocide C' and 'Biocide D' prepared according to the method of the present invention to those of 'Biocide A' and 'Biocide B', after collecting river water (pH 7.8), the prepared biocides were tested for antibacterial activities upon addition to a river water-containing beaker to a variety of concentrations, and total microorganism population and total halogen residual level were measured as described above. The results are shown in Tables 5 and 6.

TABLE 5

| Biocide Concentration (ppm) | | | | Number of Surviving Bacteria according to Time (CFU/ml) | | | | | |
|---|---|---|---|---|---|---|---|---|---|
| A | B | C | D | 5 min | 30 min | 1 hr | 2 hrs | 12 hrs | 24 hrs |
| 50 | | | | 600,000 | 400,000 | 300,000 | 300,000 | 400,000 | 400,000 |
| 100 | | | | 200,000 | 100,000 | 80,000 | 50,000 | 40,000 | 60,000 |
| 150 | | | | 80,000 | 40,000 | 10,000 | 8,000 | 5,000 | 7,000 |
| 200 | | | | 10,000 | 20,000 | 10,000 | 6,000 | 3,000 | 1,000 |
| 250 | | | | 8,000 | 1,000 | 0 | 0 | 0 | 0 |
| | 50 | | | 1,000,000 | 800,000 | 600,000 | 700,000 | 800,000 | 900,000 |
| | 100 | | | 500,000 | 300,000 | 400,000 | 300,000 | 400,000 | 400,000 |
| | 150 | | | 300,000 | 100,000 | 20,000 | 80,000 | 100,000 | 90,000 |
| | 200 | | | 100,000 | 80,000 | 40,000 | 30,000 | 10,000 | 10,000 |
| | 250 | | | 10,000 | 4,000 | 3,000 | 1,000 | 2,000 | 1,000 |
| | | 50 | | 1,000,000 | 800,000 | 700,000 | 500,000 | 300,000 | 200,000 |
| | | 100 | | 500,000 | 200,000 | 100,000 | 80,000 | 60,000 | 70,000 |
| | | 150 | | 200,000 | 70,000 | 20,000 | 10,000 | 10,000 | 8,000 |
| | | 200 | | 100,000 | 50,000 | 10,000 | 2,000 | 5,000 | 3,000 |
| | | 250 | | 80,000 | 20,000 | 4,000 | 3,000 | 2,000 | 500 |
| | | | 50 | 600,000 | 400,000 | 200,000 | 150,000 | 100,000 | 100,000 |
| | | | 100 | 300,000 | 200,000 | 150,000 | 100,000 | 50,000 | 40,000 |
| | | | 150 | 100,000 | 50,000 | 30,000 | 20,000 | 30,000 | 10,000 |
| | | | 200 | 50,000 | 40,000 | 30,000 | 10,000 | 10,000 | 2,000 |
| | | | 250 | 20,000 | 10,000 | 5,000 | 6,000 | 5,000 | 100 |

TABLE 6

| Biocide Concentration (ppm) | | | | Total Halogen Residual Level according to Time (ppm) | | | | | |
|---|---|---|---|---|---|---|---|---|---|
| A | B | C | D | 5 min | 30 min | 1 hr | 2 hrs | 12 hrs | 24 hrs |
| 50 | | | | 1.35 | 1.07 | 0.87 | 0.72 | 0.43 | 0.15 |
| 100 | | | | 2.55 | 2.11 | 2.01 | 1.68 | 0.92 | 0.32 |
| 150 | | | | 3.84 | 3.24 | 3.23 | 2.48 | 1.24 | 0.38 |
| 200 | | | | 4.29 | 4.09 | 4.03 | 3.04 | 1.55 | 0.66 |
| 250 | | | | 5.23 | 5.13 | 5.08 | 3.78 | 2.23 | 0.75 |
| | 50 | | | 0.71 | 0.56 | 0.34 | 0.26 | 0.11 | 0.08 |
| | 100 | | | 1.24 | 1.11 | 0.58 | 0.34 | 0.20 | 0.14 |
| | 150 | | | 1.76 | 1.52 | 0.89 | 0.67 | 0.34 | 0.16 |
| | 200 | | | 2.23 | 2.09 | 1.23 | 0.84 | 0.47 | 0.23 |
| | 250 | | | 2.54 | 2.16 | 1.97 | 1.43 | 0.94 | 0.57 |
| | | 50 | | 2.25 | 1.98 | 1.97 | 1.72 | 1.55 | 1.49 |
| | | 100 | | 4.23 | 4.05 | 3.86 | 3.57 | 3.42 | 3.28 |
| | | 150 | | 6.46 | 5.97 | 5.79 | 5.43 | 5.05 | 5.15 |
| | | 200 | | 8.63 | 8.24 | 7.93 | 7.10 | 6.89 | 7.02 |
| | | 250 | | 9.85 | 9.34 | 9.23 | 8.92 | 8.63 | 8.59 |
| | | | 50 | 1.76 | 1.34 | 1.56 | 1.23 | 0.97 | 0.88 |
| | | | 100 | 3.24 | 2.67 | 3.23 | 2.87 | 3.07 | 2.55 |
| | | | 150 | 5.54 | 4.11 | 4.87 | 4.76 | 3.86 | 3.47 |
| | | | 200 | 7.13 | 5.67 | 6.74 | 5.27 | 5.43 | 5.32 |
| | | | 250 | 8.34 | 7.42 | 8.13 | 6.23 | 6.77 | 6.45 |

As apparent from Tables 5 and 6, when 'Biocide A' was added to river water, total halogen residual level was found to be sharply reduced with the passage of time, and after 24 hours, even upon adding 'Biocide A' to a concentration of 250 ppm, total halogen residual level was reduced to below 1 ppm. In addition, right after addition of 'Biocide A', microorganism population was sharply reduced, but, thereafter, there was no large decrease in the microorganism population. Upon 'Biocide A' being added to a concentration of 150 ppm, viable bacteria was rarely detected even shortly after addition. On the whole, like other oxidizing biocides, 'Biocide A' has a strong initial antibacterial activity, but has low durability, due to the rapid reduction in total halogen residual level. Therefore, 'Biocide A' is very effective in non-circulating water systems such as a beaker where contamination of microorganisms rarely occurs. However, in circulating water systems, which are exposed to contamination sources such as microorganisms, it is required for 'Biocide A' to be added in a great quantity to keep the biocide at an effective level, causing the increase of pH in applied water systems, corrosiveness, and economic loss.

Because 'Biocide B' was prepared using a small amount of hypochlorite serving as an effective ingredient, and gaseous chlorine was formed during its preparation, resulting in the effective ingredient being in a small amount, microorganism populations were not remarkably reduced by 'Biocide B' at less than 150 ppm, and the content of total halogen residual was also dropped immediately, confirming that a great quantity of stabilized hypobromite is already formed before application to river water, which is similar to results obtained using 'Biocide A'. Therefore, an excessive quantity of 'Biocide B' should be added in order to exhibit an effective disinfection activity against microorganisms, resulting in difficult preparation and high cost.

Upon adding 'Biocide C', in the initial stage, there was no large reduction in microorganism population, but a remarkable reduction was seen with the passage of time. Such a result from 'Biocide C' is unique in comparison with general properties of conventional oxidizing biocides. Generally, oxidizing biocides show a proportional relationship between initial concentration and biocidal activity, and their rapid consumption upon exposure to impurities in water or air. However, although 'Biocide C' is an oxidizing biocide composed of stabilized hypochlorite and water-soluble bromide ion, it displayed enhanced biocidal activity with the passage of time, indicating that a compound having disinfection activity was continuously produced in water after its addition. This finding was further demonstrated from its lower consumption rate of halogen residual than that of Biocides 'A' and 'B', resulting from the fact that stabilized hypochlorite in water continuously releases available chlorine, which reacts with bromide ion to generate stabilized hypobromite, whereas Biocides 'C' and 'D', which already contain a great quantity stabilized hypobromite, can provide high initial disinfection activity, but their effective ingredient is rapidly consumed. This kind of phenomena was also observed in a pilot cooling water tower test, as will be described below, in which biocides 'A' and 'B' displayed larger consumption in total halogen residual than 'Biocide C'. Thereby, 'Biocide C', which is characterized by continuously increased biocidal activity and durability of biocidal activity even after 1 day, despite low initial biocidal activity, may be very effective in practical applications such as cooling towers of plants or paper-making processes, with its largely reduced addition amount.

Upon adding 'Biocide D', as apparent in Table 5, initial microorganism population was greatly reduced to a level lower than after addition of 'Biocide C' and to a level higher than after addition of 'Biocide A', and as shown in Table 6, consumption rate in halogen residual was found to be faster than that of 'Biocide C' and slower than that of 'Biocide A', indicating that its durability is much better than that of 'Biocide A' and slightly less than that of 'Biocide C'. 'Biocide D' is characterized by preparation with no generation of gas including chlorine, and effective initial biocidal activity, namely, fast-acting ability, as well as durability.

Upon comparing results from Biocides 'C' and 'D', of which preparation processes were the same, excepting that 'Biocide D' is prepared by lowering pH of 'Biocide C' using an acidic solution and then raising the pH to 13.5 using a alkali solution, and characterized by the formation of stabilized hypobromite before application to water systems, like Biocides 'A' and 'B', it was found that effective initial biocidal activity and durability of 'Biocide C' can be controlled by changing in its pH value. Moreover, the level of hypobromite formed before application to water systems may vary depending on a pH value lowered by an acidic solution and the length of time the lowered pH is maintained.

Example 4

A sodium hypochlorite solution (I), sulfamic acid (II), and sodium bromide (III) as a bromide ion source were added separately to a water system, or in the mixed form of two ingredients to water systems. A stabilized hypochlorite solution (I+II), which was prepared by dissolving sodium hypochlorite in a alkali solution having a pH over 11 and adding sulfamic acid to the solution, and a 45% sodium bromide solution were added to a water system. A mixture (II+III), prepared by dissolving sulfamic acid in water and adding a 45% sodium bromide solution to the solution, and hypochlorite, were added to a water system. Total halogen residual level and microorganism population were measured, and the results are shown in Tables 7 and 8.

TABLE 7

| Biocide Concentration (ppm) | | | | | | | Total Halogen Residual Level (ppm) | | | | Remarks |
|---|---|---|---|---|---|---|---|---|---|---|---|
| I + II | III | II + III | I | I | II | III | 5 min | 1 hr | 2 hrs | 24 hrs | (ppm) |
| 8 | 0.7 | | | | | | 2.13 | 2.03 | 1.67 | 1.53 | II: |
| 8 | 4.6 | | | | | | 1.87 | 1.67 | 1.49 | 0.78 | 4.8 |
| 16 | 1.4 | | | | | | 4.03 | 3.76 | 3.47 | 3.06 | II: |
| 16 | 9.2 | | | | | | 3.74 | 3.29 | 2.96 | 1.56 | 9.6 |
| 24 | 2.0 | | | | | | 6.34 | 5.92 | 5.34 | 5.03 | II: |
| 24 | 13.9 | | | | | | 5.58 | 5.14 | 4.95 | 2.97 | 14.4 |
| 32 | 2.7 | | | | | | 8.55 | 7.67 | 6.99 | 7.02 | II: |
| 32 | 18.5 | | | | | | 7.56 | 6.98 | 6.34 | 3.79 | 19.3 |
| 40 | 3.4 | | | | | | 9.67 | 9.02 | 8.88 | 8.49 | II: |
| 40 | 23.1 | | | | | | 8.78 | 8.24 | 7.74 | 5.04 | 24.0 |
| | | 5.5 | 3.2 | | | | 1.67 | 1.58 | 1.22 | 1.08 | II: |
| | | 9.4 | 3.2 | | | | 1.45 | 1.13 | 0.85 | 0.42 | 4.8 |
| | | 11.0 | 6.4 | | | | 3.11 | 2.89 | 2.74 | 2.23 | II: |
| | | 16.0 | 6.4 | | | | 2.76 | 2.43 | 2.11 | 0.79 | 9.6 |
| | | 16.4 | 9.9 | | | | 4.31 | 4.12 | 3.87 | 3.55 | II: |
| | | 28.3 | 9.9 | | | | 4.11 | 3.67 | 3.04 | 1.23 | 14.4 |
| | | 22.0 | 12.8 | | | | 6.43 | 5.67 | 4.95 | 4.62 | II: |
| | | 37.8 | 12.8 | | | | 5.11 | 4.50 | 4.03 | 1.67 | 19.3 |
| | | 27.4 | 16.0 | | | | 7.32 | 6.56 | 6.32 | 6.11 | II: |
| | | 47.1 | 16.0 | | | | 6.07 | 5.45 | 4.67 | 2.21 | 24.0 |
| | | | | 3.2 | 4.8 | 0.7 | 1.71 | 1.52 | 1.18 | 0.96 | |
| | | | | 6.4 | 9.6 | 9.2 | 2.83 | 2.33 | 1.61 | 0.84 | |
| | | | | 12.8 | 19.3 | 2.7 | 6.22 | 5.43 | 4.88 | 4.34 | |
| | | | | 16.0 | 24.0 | 23.1 | 5.93 | 5.29 | 4.51 | 2.32 | |

Note:
I: Addition amount of sodium hypochlorite to water retained in a water system
II: Addition amount of sulfamic acid to water retained in a water system
III: Addition amount of sodium bromide to water retained in a water system

TABLE 8

| Biocide and its Addition Amount (ppm) | | | | | | | Number of Survival Bacteria (CFU/ml) × $10^3$ | | | | Remarks |
|---|---|---|---|---|---|---|---|---|---|---|---|
| I + II | III | II + III | I | I | II | III | 5 min | 1 hr | 2 hrs | 24 hrs | (ppm) |
|  |  |  |  |  |  |  |  |  |  | 1,700 |  |
| 8 | 0.7 |  |  |  |  |  | 1,100 | 200 | 50 | 20 | II: |
| 8 | 4.6 |  |  |  |  |  | 800 | 150 | 30 | 10 | 4.8 |
| 16 | 1.4 |  |  |  |  |  | 400 | 40 | 10 | 1 | II: |
| 16 | 9.2 |  |  |  |  |  | 400 | 30 | 5 | 0.5 | 9.6 |
| 24 | 2.0 |  |  |  |  |  | 300 | 50 | 2 | 0.2 | II: |
| 24 | 13.9 |  |  |  |  |  | 300 | 20 | 0.6 | 0.1 | 14.4 |
| 32 | 2.7 |  |  |  |  |  | 150 | 10 | 3 | 0 | II: |
| 32 | 18.5 |  |  |  |  |  | 100 | 3 | 0.5 | 0 | 19.3 |
| 40 | 3.4 |  |  |  |  |  | 120 | 5 | 0 | 0 | II: |
| 40 | 23.1 |  |  |  |  |  | 10 | 0.2 | 0 | 0 | 24.0 |
|  |  | 5.5 | 3.2 |  |  |  | 1,000 | 500 | 200 | 100 | II: |
|  |  | 9.4 | 3.2 |  |  |  | 900 | 300 | 150 | 200 | 4.8 |
|  |  | 11.0 | 6.4 |  |  |  | 400 | 300 | 100 | 50 | II: |
|  |  | 16.0 | 6.4 |  |  |  | 300 | 200 | 80 | 20 | 9.6 |
|  |  | 16.4 | 9.9 |  |  |  | 300 | 100 | 100 | 30 | II: |
|  |  | 28.3 | 9.9 |  |  |  | 200 | 50 | 50 | 10 | 14.4 |
|  |  | 22.0 | 12.8 |  |  |  | 200 | 80 | 50 | 10 | II: |
|  |  | 37.8 | 12.8 |  |  |  | 150 | 20 | 10 | 5 | 19.3 |
|  |  | 27.4 | 16.0 |  |  |  | 100 | 50 | 20 | 0 | II: |
|  |  | 47.1 | 16.0 |  |  |  | 60 | 10 | 5 | 0 | 24.0 |
|  |  |  |  | 3.2 | 4.8 | 0.7 | 1,200 | 1,000 | 500 | 300 |  |
|  |  |  |  | 6.4 | 9.6 | 9.2 | 300 | 300 | 200 | 50 |  |
|  |  |  |  | 12.8 | 19.3 | 2.7 | 200 | 100 | 50 | 0 |  |
|  |  |  |  | 16.0 | 24.0 | 23.1 | 100 | 50 | 20 | 0 |  |

Note:
I: Addition amount of sodium hypochlorite to water retained in a water system
II: Addition amount of sulfamic acid to water retained in a water system
III: Addition amount of sodium bromide to water retained in a water system The case that stabilized hypochlorite solution (I+II) and the bromide ion source were added individually, not in the mixed form, gave a similar result to 'Biocide C' (refer to Tables 5 and 6), indicating the stabilized hypochlorite solution having a pH over 11 prepared by reacting sodium hypochlorite with sulfamic acid displayed biocidal activity in the presence of bromide ion in water regardless of a addition method of the bromide ion. That is, a mixture of stabilized hypochlorite and a water-soluble bromide ion source may have a similar biocidal activity in water systems as when they are added separately. This finding indicates that stabilized hypochlorite does not react with water-soluble bromide ion in an environment of pH over 11.

In contrast, in the case that a mixture solution of sulfamic acid and bromide ion (II+III) and a hypochlorite solution were added to a water system, the content of total halogen residual was, as apparent in Table 7, found to be rapidly reduced in comparison with the case in which the sodium hypochlorite (I+II) stabilized by sulfamic acid was added. Such a finding is based on the fact that hypochlorite, which is volatile, was partially volatilized in part before stabilization, and reacts with bromide ion to form hypobromite in water systems having a pH about 8, resulting in the large reduction in total halogen residual level. Upon increasing the addition amount of bromide ion, total halogen residual level was also observed to be greatly reduced, due to increased formation of stabilized hypobromite, which is more volatile than stabilized hypochlorite in the same manner as described above. This result was identical to the finding that the total halogen residual of 'Biocide A' is consumed more rapidly than that of 'Biocide C'.

As apparent in Table 7, when a hypochlorite solution, sulfamic acid, and sodium bromide ion were separately added to a water system with no stabilization of hypochlorite by sulfamic acid, the total halogen residual level was similar to the case where a mixture of sulfamic acid and bromide ion source (I+II) and a sodium hypochlorite solution were added.

On a whole, it was demonstrated from the data in Table 7 that the content of total halogen residual could be slowly reduced by adding hypochlorite separately or in a mixture with a bromide ion source to a water system after stabilization at pH over 11 using sulfamic acid.

Table 8 shows the biocidal activities against microorganisms according to the above-described addition methods of a hypochlorite solution, sulfamic acid, and a bromide ion source. When a stabilized hypochlorite solution (I+II) was added individually or in a mixture with bromide ion, it was found to be low in initial biocidal activity, but excellent in durability, with increase in consumption rate of total halogen residual upon increasing the addition amount of the bromide ion source. Such a result is believed to result from increased content of hypobromite, which was formed by the reaction of available chlorine released from the stabilized hypochlorite with water-soluble bromide ion.

Upon adding a hypochlorite solution in an unstabilized form to a water system, similar results were obtained when adding unstabilized hypochlorite and a bromide ion source to a water system, despite they are added individually or as a mixture. Also, when using stabilized hypochlorite, similar results are also obtained, except that a large amount of sodium hypochlorite is consumed. Namely, 5 minutes after addition, the viable microorganism population was similar, but, with the passage of time, consumption rate of total halogen residual increased owing to the volatility of unstabilized hypochlorite, thus numbers of viable microorganisms remaining high.

Considering these results together, when hypochlorite is stabilized by sulfamic acid, consumption of total halogen residual decreases with the passage of time, thus the biocidal activity having excellent durability. In contrast, upon unstabilized hypochlorite being added to water systems containing a stabilizer, more hypochlorite may be consumed than when adding hypochlorite after stabilization. After being stabilized, hypochlorite applied separately with bromide ion may have similar biocidal activity as when it is added in a mixed form with bromide ion. Further, as more bromide ion is used with the stabilized hypochlorite, the content of total halogen residual in water is lowered, while initial biocidal activity is enhanced.

Example 5

In order to investigate the disinfection efficiency of the biocides, a pilot cooling tower test was conducted. A pilot cooling tower was prepared containing water of 120 kg of water and a circulating water at 1,600 kg/hr adjusted to pH 7.8±2, and undergoing water temperature change by evaporation of not over 5° C. Concentration ratio of the recirculating water was adjusted to 6 by controlling effluence amount of water to 2.8 kg/hr. In addition, PBTC and polymer were continuously added to the water to a level of 6 and 10 ppm, respectively, to prevent corrosion and scale, the pilot cooling tower was operated for at least 1 day before addition of biocides while being maintained at 35±2° C. The river water used for the tests contained calcium hardness of 41 ppm and M-alkalinity of 20 ppm, all as calcium carbonated.

Herein, the total amount of biocide to be added was supplied at one time to the pilot cooling tower with the consideration of water retained therein, and scale and corrosion inhibitors were sequentially added.

Biocides 'A', 'B', 'C', and 'D' prepared as describe above were used, and the content of total halogen residual and the number of surviving bacteria were measured. The results are given in Tables 9 and 10, below.

TABLE 9

| Biocide & Concentration (ppm) | | | | Total Halogen Residual Level according to Time (ppm) | | | | | |
| --- | --- | --- | --- | --- | --- | --- | --- | --- | --- |
| A | B | C | D | 5 min | 30 min | 1 hr | 2 hrs | 12 hrs | 24 hrs |
| 50 | | | | 1.23 | 0.66 | 0.45 | 0.38 | 0.15 | 0.01 |
| 100 | | | | 2.45 | 1.23 | 1.12 | 0.88 | 0.31 | 0.11 |
| 150 | | | | 3.56 | 1.88 | 1.73 | 1.45 | 0.54 | 0.14 |
| 200 | | | | 4.11 | 2.23 | 2.21 | 1.64 | 0.68 | 0.18 |
| 250 | | | | 5.34 | 2.95 | 2.77 | 1.96 | 1.11 | 0.23 |
| | 50 | | | 0.67 | 0.28 | 0.18 | 0.12 | 0.03 | 0.01 |
| | 100 | | | 1.21 | 0.57 | 0.31 | 0.16 | 0.07 | 0.05 |
| | 150 | | | 1.69 | 0.91 | 0.49 | 0.34 | 0.11 | 0.05 |
| | 200 | | | 2.13 | 1.12 | 0.78 | 0.45 | 0.17 | 0.1 |
| | 250 | | | 2.44 | 1.31 | 1.08 | 0.87 | 0.39 | 0.16 |
| | | 50 | | 2.11 | 1.18 | 1.05 | 0.89 | 0.66 | 0.43 |
| | | 100 | | 4.19 | 2.35 | 2.03 | 1.91 | 1.42 | 1.06 |
| | | 150 | | 6.19 | 3.45 | 3.29 | 2.98 | 2.19 | 1.67 |
| | | 200 | | 8.55 | 4.86 | 4.54 | 3.97 | 3.10 | 2.32 |
| | | 250 | | 9.27 | 5.47 | 5.25 | 4.91 | 3.68 | 2.90 |
| | | | 50 | 1.74 | 0.68 | 0.86 | 0.66 | 0.36 | 0.26 |
| | | | 100 | 3.22 | 1.41 | 1.83 | 1.52 | 1.33 | 0.84 |
| | | | 150 | 5.29 | 2.32 | 2.67 | 2.67 | 1.71 | 1.22 |
| | | | 200 | 7.04 | 3.26 | 3.80 | 2.89 | 2.43 | 1.76 |
| | | | 250 | 8.15 | 4.38 | 4.63 | 3.41 | 3.01 | 2.17 |

TABLE 10

| Biocide & Concentration (ppm) | | | | Number of Surviving Bacteria according to Time (CFU/ml) | | | | | |
| --- | --- | --- | --- | --- | --- | --- | --- | --- | --- |
| A | B | C | D | 5 min | 30 min | 1 hr | 2 hrs | 12 hrs | 24 hrs |
| 0 | | | | | | | | | 2,000 |
| 50 | | | | 800 | 500 | 400 | 200 | 500 | 700 |
| 100 | | | | 300 | 400 | 300 | 100 | 300 | 500 |
| 150 | | | | 100 | 200 | 100 | 60 | 130 | 300 |
| 200 | | | | 50 | 10 | 0.3 | 0.1 | 100 | 300 |
| 250 | | | | 10 | 0.4 | 0.1 | 0.1 | 40 | 400 |
| | 50 | | | 1,500 | 1,400 | 1,200 | 1,600 | 1,400 | 1,500 |
| | 100 | | | 1,200 | 1,000 | 800 | 1,400 | 1,600 | 1,400 |
| | 150 | | | 800 | 500 | 900 | 1,200 | 1,700 | 2,000 |
| | 200 | | | 400 | 300 | 100 | 200 | 800 | 1,500 |
| | 250 | | | 100 | 50 | 20 | 30 | 30 | 500 |
| | | 50 | | 1,300 | 1,000 | 600 | 400 | 300 | 500 |
| | | 100 | | 1,000 | 800 | 500 | 300 | 200 | 200 |
| | | 150 | | 500 | 300 | 200 | 200 | 80 | 50 |
| | | 200 | | 300 | 200 | 100 | 50 | 30 | 10 |
| | | 250 | | 200 | 200 | 100 | 40 | 10 | 5 |
| | | | 50 | 1,000 | 500 | 1,000 | 1,200 | 1,500 | 1,400 |
| | | | 100 | 400 | 200 | 100 | 40 | 80 | 100 |
| | | | 150 | 200 | 100 | 40 | 30 | 60 | 60 |
| | | | 200 | 100 | 50 | 30 | 10 | 20 | 10 |
| | | | 250 | 50 | 10 | 0.5 | 0.3 | 1 | 3 |

When the pilot cooling tower was operated under the condition described above, after 1 day, the 43% of added biocide was lost to the exterior, and cooling water contacted continuously with air, thus introducing organic materials from the air. Hypochlorite stabilized before or after addition to the pilot cooling water system was volatilized at a low rate owing to the continuous circulation of cooling water, which slower than volatilization of unstabilized hypochlorite, leading to the increase in consumption of total halogen residual to a level slightly higher than the beaker test with the results in Table 6. As apparent in Table 9, upon adding the biocide 'A' or 'B' even up to 250 ppm, after 1 day, it was observed that most of available halogen was consumed, requiring its continuous addition to supply constant disinfection efficiency, and thus resulting in the increase in its addition amount. In contrast, even after 1 day, in the pilot cooling tower treated with the biocides 'C' and 'D', total halogen residual was maintained at a level effective for killing bacteria, thereby making it possible to add them once per day, although their continuous addition is also possible. Therefore, it may be effective for the biocides 'C' or 'D' to be added at an initial stage of operation of small cooling towers and highly contaminated cooling towers.

Referring to Table 10 showing the number of surviving bacteria according to time, microorganism population was higher than the data in Table 5, which is consistent with the finding that total halogen residual level was relatively reduced due to contact of cooling water with external air. Considering the above results together, the biocides 'A' and 'B' can provide durability of biocidal activity in non-circulating water systems such as a beaker environment in Example 3, but not in circulating water systems such as cooling towers, where continuous contact of water with external air occurs, causing a large reduction in total halogen residual level owing to the loss of volatile hypochlorite and impurities introduced from the exterior, and thus requiring addition of large quantities of the biocides. Especially, the biocide 'B' contains an effective ingredient in a relatively low amount because of gas generation, including gaseous chlorine, during its preparation, thereby, upon being used in water systems, the content of total halogen residual becomes rapidly reduced, thereby requiring increased dosage, and thereby making it difficult to apply to industrial water systems.

On the other hand, the biocide 'C' showed low antibacterial activity in an initial stage, but, as time passed, excellent bactericidal activity, with a large reduction in the number of surviving bacteria, while maintaining its antibacterial activity even after 24 hours. The biocide 'D' was inferior in initial antibacterial activity, but superior in its durability to the biocide 'A'. The biocide 'D' was superior in initial antibacterial activity, but slightly inferior in durability to the biocide 'C'.

Example 6

With the use of the same pilot cooling tower conditions as in Example 5, the biocides 'A', 'B', 'C', and 'D' were continuously added using a pump, and the addition amounts of the biocides for day 1 are given in Table 11, below. The biocides were added to a level of 50 ppm to water contained in the pilot cooling towers, excepting the biocide 'D' being added up to 100 ppm. The content of total halogen residual was maintained at 1±0.2 ppm, and the addition amounts of the biocides were measured for day 1. If the pilot cooling towers had been contaminated with slime, this may have affected the addition amount of the biocides. To remove such a possibility, slime was completely eliminated before the test.

TABLE 11

| | | Biocide | | | |
| --- | --- | --- | --- | --- | --- |
| | | A | B | C | D |
| Total Addition Amount for first 24 hrs (g) | | 68 | 71 | 20 | 31 |
| Number of Surviving Bacteria (CFU/ml) | Before addition | 2,000,000 | | | |
| | After 6 hrs | 40,000 | 70,000 | 400,000 | 100,000 |
| | After 12 hrs | 50,000 | 50,000 | 100,000 | 60,000 |
| | After 24 hrs | 40,000 | 60,000 | 50,000 | 40,000 |

In comparison with the data from Example 3, it was found that the biocides were more rapidly consumed in the pilot cooling towers. Especially, the addition amount of the biocides 'A' and 'B' was higher than the biocides 'C' and 'D'. This is believed to result from the fact that the non-circulating water system was used in Example 3, whereas the continuous contact with external air occurred in the pilot cooling tower, and that the biocides 'A' and 'B' are more volatile than the biocides 'C' and 'D'.

Referring to the number of surviving bacteria in Table 11, in the cases of the biocides 'A', 'B', and 'D', microorganism population was reduced to a suitable level after 6 hours, whereas the biocide 'C' showed a reduction pattern starting at 6 hours after addition and reaching a suitable level after 24 hours, which coincides with the data from Example 3. On the whole, the biocide 'C' was slightly lower in its initial biocidal activity, but excellent in durability, as well as being low in its consumption rate. Biocide 'D' had a durability slightly lower than Biocide 'C', but better than biocides 'A' and 'B', as well as higher initial biocidal activity.

Example 7

As described in Example 4, hypochlorite, a stabilizer, and sodium bromide were added separately or as a mixture to a pilot cooling tower, in which the addition was conducted all at once, while organic phosphate as a corrosion inhibitor and polymer as a scale inhibitor were separately added.

The pilot cooling tower contained 120 kg of water, had a circulation rate of 1,600 kg/hr, and was adjusted to pH 7.8±2, and water temperature change according to evaporation was not over 5° C. Concentration ratio of water was adjusted to 6 by controlling effluence amount of water to 2.8 kg/hr. In addition, PBTC and polymer were continuously added to a level of 6 and 10 ppm, respectively, to prevent corrosion and scale, formation, and the pilot cooling tower was operated before at least 1 day of addition of biocides while being maintained at 35±2° C. The river water used for the tests contained calcium hardness of 41 ppm and M-alkalinity of 20 ppm, all as calcium carbonate.

In Tables 12 and 13, below, the resulting total halogen residual level and the number of surviving bacteria according to time are shown.

TABLE 12

| Biocide Concentration (ppm) | | | | | | | Total Halogen Residual Level (ppm) | | | | Remarks |
|---|---|---|---|---|---|---|---|---|---|---|---|
| I + II | III | II + III | I | I | II | III | 5 min | 1 hr | 2 hrs | 24 hrs | (ppm) |
| 8 | 0.7 | | | | | | 1.89 | 1.33 | 0.79 | 0.41 | II: |
| 8 | 4.6 | | | | | | 1.61 | 1.05 | 0.66 | 0.25 | 4.8 |
| 16 | 1.4 | | | | | | 3.22 | 2.57 | 1.79 | 0.93 | II: |
| 16 | 9.2 | | | | | | 3.08 | 2.25 | 1.38 | 0.51 | 9.6 |
| 24 | 2.0 | | | | | | 5.62 | 4.02 | 2.67 | 1.66 | II: |
| 24 | 13.9 | | | | | | 5.12 | 3.18 | 2.23 | 0.93 | 14.4 |
| 32 | 2.7 | | | | | | 7.51 | 4.87 | 3.21 | 2.20 | II: |
| 32 | 18.5 | | | | | | 6.78 | 4.26 | 2.98 | 1.06 | 19.3 |
| 40 | 3.4 | | | | | | 8.11 | 5.78 | 4.43 | 2.72 | II: |
| 40 | 23.1 | | | | | | 7.78 | 5.21 | 3.52 | 1.84 | 24.0 |
| | | 5.5 | 3.2 | | | | 1.43 | 0.93 | 0.56 | 0.32 | II: |
| | | 9.4 | 3.2 | | | | 1.27 | 0.67 | 0.38 | 0.17 | 4.8 |
| | | 11.0 | 6.4 | | | | 2.63 | 1.69 | 1.26 | 0.59 | II: |
| | | 16.0 | 6.4 | | | | 2.38 | 1.45 | 1.10 | 0.23 | 9.6 |
| | | 16.4 | 9.9 | | | | 3.77 | 2.53 | 1.81 | 1.06 | II: |
| | | 28.3 | 9.9 | | | | 3.59 | 2.25 | 1.42 | 0.31 | 14.4 |
| | | 22.0 | 12.8 | | | | 5.61 | 3.47 | 2.27 | 2.27 | II: |
| | | 37.8 | 12.8 | | | | 4.39 | 2.70 | 1.96 | 0.49 | 19.3 |
| | | 27.4 | 16.0 | | | | 6.49 | 4.16 | 2.96 | 1.73 | II: |
| | | 47.1 | 16.0 | | | | 5.33 | 3.23 | 2.09 | 0.57 | 24.0 |
| | | | | 3.2 | 4.8 | 0.7 | 1.25 | 0.83 | 0.52 | 0.20 | |
| | | | | 6.4 | 9.6 | 9.2 | 2.24 | 1.29 | 0.76 | 0.19 | |
| | | | | 12.8 | 19.3 | 2.7 | 4.87 | 2.82 | 1.99 | 0.87 | |
| | | | | 16.0 | 24.0 | 23.1 | 4.84 | 2.70 | 1.76 | 0.55 | |

Note:
I: Addition amount of sodium hypochlorite to water retained in a water system
II: Addition amount of sulfamic acid to water retained in a water system
III: Addition amount of sodium bromide to water retained in a water system

TABLE 13

| Biocide Concentration (ppm) | | | | | | | Number of Surviving Bacteria (CFU/ml) × 10³ | | | | Remarks |
|---|---|---|---|---|---|---|---|---|---|---|---|
| I + II | III | II + III | I | I | II | III | 5 min | 1 hr | 2 hrs | 24 hrs | (ppm) |
| | | | | | | | | | | 1,700 | |
| 8 | 0.7 | | | | | | 1,100 | 200 | 50 | 20 | II: |
| 8 | 4.6 | | | | | | 800 | 150 | 30 | 10 | 4.8 |
| 16 | 1.4 | | | | | | 400 | 40 | 10 | 1 | II: |
| 16 | 9.2 | | | | | | 400 | 30 | 5 | 0.5 | 9.6 |
| 24 | 2.0 | | | | | | 300 | 50 | 2 | 0.2 | II: |
| 24 | 13.9 | | | | | | 300 | 20 | 0.6 | 0.1 | 14.4 |
| 32 | 2.7 | | | | | | 150 | 10 | 3 | 0 | II: |
| 32 | 18.5 | | | | | | 100 | 3 | 0.5 | 0 | 19.3 |
| 40 | 3.4 | | | | | | 120 | 5 | 0 | 0 | II: |
| 40 | 23.1 | | | | | | 10 | 0.2 | 0 | 0 | 24.0 |
| | | 5.5 | 3.2 | | | | 1,000 | 500 | 200 | 100 | II: |
| | | 9.4 | 3.2 | | | | 900 | 300 | 150 | 200 | 4.8 |
| | | 11.0 | 6.4 | | | | 400 | 300 | 100 | 50 | II: |
| | | 16.0 | 6.4 | | | | 300 | 200 | 80 | 20 | 9.6 |
| | | 16.4 | 9.9 | | | | 300 | 100 | 50 | 30 | II: |
| | | 28.3 | 9.9 | | | | 200 | 50 | 50 | 10 | 14.4 |
| | | 22.0 | 12.8 | | | | 200 | 80 | 50 | 10 | II: |
| | | 37.8 | 12.8 | | | | 150 | 20 | 10 | 5 | 19.3 |
| | | 27.4 | 16.0 | | | | 100 | 50 | 20 | 0 | II: |
| | | 47.1 | 16.0 | | | | 60 | 10 | 5 | 0 | 24.0 |
| | | | | 3.2 | 4.8 | 0.7 | 1,200 | 1,000 | 500 | 300 | |
| | | | | 6.4 | 9.6 | 9.2 | 300 | 300 | 200 | 50 | |
| | | | | 12.8 | 19.3 | 2.7 | 200 | 100 | 50 | 0 | |
| | | | | 16.0 | 24.0 | 23.1 | 100 | 50 | 20 | 0 | |

Note:
I: Addition amount of sodium hypochlorite to water retained in a water system
II: Addition amount of sulfamic acid to water retained in a water system
III: Addition amount of sodium bromide to water retained in a water system The data in Tables 12 and 13 show an identical pattern to the data from Example 4. When a stabilized sodium hypochlorite solution (I+II) prepared using a stabilizer before addition was added to the pilot cooling tower, the content of total halogen residual was reduced in a slower manner than the case where a mixture solution (II+III) comprising a stabilizer and sodium bromide ion and sodium hypobromite were individually added. Thereby, it was demonstrated that hypochlorite stabilized by sulfamic acid before addition may be more effective than hypochlorite stabilized in the pilot cooling tower. This result is partially due to the rapid loss of highly volatile unstabilized hypochlorite.

Upon increasing the addition amount of bromide ion, it was found that the total halogen residual level dropped, whereas the number of surviving microorganisms dropped sharply, indicating that the enhanced initial biocidal activity and the reduced durability was obtained as a result of the increase in hypobromite formation.

There was no difference in the content of total halogen residual and the number of surviving bacteria among all the cases where each ingredient was added individually or in a mixed state.

INDUSTRIAL APPLICABILITY

As described hereinbefore, when a biocide is prepared according to the method of the present invention, the expensive bromide ion source can be used in a greatly reduced amount, in comparison with the conventional biocides. In addition, the method of the present invention can provide a stabilized biocide having enhanced durability of its biocidal activity as well as excellent initial biocidal activity.

The invention claimed is:

1. A method of controlling the growth of microorganisms, comprising the steps of:

(a) preparing stabilized alkali or alkaline earth metal hypochlorite having a pH at least 11 by mixing a chlorine oxidant including alkali or alkaline earth metal hypochlorite with a stabilizer selected from the group consisting of acid amide derivatives of carbonic acids, carboxylic acids, amino acids, and sulfuric acids in an alkali solution;

(b) preparing a bromide ion source; and (c) sequentially or simultaneously introducing the stabilized alkali or alkaline earth metal hypoclilorite prepared in step (a) and the bromide ion source prepared in step (b) into a habitat of microorganisms up to 0.1 to 10 ppm total halogen residual.

2. The method as set forth in claim 1, wherein the stabilized hypochlorite and the bromide ion source is added to a habitat of microorganisms to 0.2 to 5 ppm total halogen residual.

3. The method as set forth in claim 1 or claim 2, wherein the water system is selected from the group consisting of swimming pools, hot springs, ponds, water slides, and industrial water systems, such as cooling towers of buildings or plants, paper-making processes, wastewater recycling systems, gas scrubber systems, freshwater systems, or air washer systems.

* * * * *

UNITED STATES PATENT AND TRADEMARK OFFICE
CERTIFICATE OF CORRECTION

PATENT NO. : 7,341,671 B2 Page 1 of 1
APPLICATION NO. : 10/506384
DATED : March 11, 2008
INVENTOR(S) : Shim et al.

It is certified that error appears in the above-identified patent and that said Letters Patent is hereby corrected as shown below:

Column 24, line 4, Claim 1, "hypochiorite" should read -- hypochlorite --

Column 24, line 11, Claim 1, "hypoclilorite" should read -- hypochlorite --

Signed and Sealed this

Twelfth Day of August, 2008

JON W. DUDAS
*Director of the United States Patent and Trademark Office*